US00PP27066P3

(12) United States Plant Patent
Bradford

(10) Patent No.: US PP27,066 P3
(45) Date of Patent: Aug. 16, 2016

(54) INTERSPECIFIC TREE NAMED 'PLUMRED XI'

(50) Latin Name: ***Prunus* sp.**
Varietal Denomination: Plumred XI

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 99 days.

(21) Appl. No.: 14/544,245

(22) Filed: Dec. 15, 2014

(65) Prior Publication Data

US 2016/0174431 P1 Jun. 16, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP21,051 P2 6/2010 Bradford

*Primary Examiner* — Susan McCormick Ewoldt

(57) ABSTRACT

The present invention relates to an interspecific tree and more particularly to a new and distinct variety broadly characterized by a medium size, medium to weak vigor, hardy, and very productive tree. Being self-unfruitful, the present variety requires cross pollination from an apricot, interspecific, or plum tree that blooms during the late season. The present variety produces a moderate amount of blossoms with sufficient pollen to entice good bee activity to facilitate pollination. The fruit matures under the ecological conditions described during late July, with first picking on Jul. 24, 2014. The fruit is uniformly medium in size, mostly red in skin color with moderate freckling, clingstone in type, globose to oblate in shape, mostly orange in flesh color, firm in texture, typically 19 brix, and good in flavor.

1 Drawing Sheet

Botanical classification: *Prunus* sp.
Varietal denomination: 'PLUMRED XI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'Plumred XI'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2000 I covered a group of six different plum trees and crossed them in this manner. To pollinate these isolated plum trees I selected bouquets from several sources of apricot and interspecific plum-apricot hybrid trees without keeping specific written details. Upon reaching maturity the fruit from these plum trees was harvested and the seeds were removed, cracked, stratified and germinated as a group with the label 'H3'. They were grown as seedlings on their own root in my greenhouse and upon reaching dormancy transplanted to a cultivated area of my experimental orchard located near Le Grand, Calif. in Merced County (San Joaquin Valley). During the spring of 2006 the claimed variety was selected by me as a single plant from the group of seedlings described above. Subsequent to origination of the present variety of interspecific tree, I asexually reproduced it by budding and grafting in the experimental orchard described above, and such reproductions were true to the original tree in all respects. The reproduction of the variety included the use of 'Nemaguard' (unpatented) rootstock upon which the present variety was true to type.

The present variety is most similar to, 'Plumred VI' (U.S. Plant Pat. No. 21,051) interspecific tree, by being self-unfruitful, by blooming during the late season, and by producing fruit that is mostly globose in shape, clingstone in type, medium in size, good in flavor, and red in skin color, but is distinguished therefrom by producing fruit that is mostly orange instead of red in flesh color and that matures about fourteen days later.

SUMMARY OF VARIETY

The present interspecific variety is characterized by a medium size, medium to weak vigor, hardy, and very productive tree. Being self-unfruitful, the present variety requires cross pollination from an apricot, interspecific, or plum tree that blooms during the late season. The present variety produces a moderate amount of blossoms with sufficient pollen to entice good bee activity to facilitate pollination. The fruit matures under the ecological conditions described during late July, with first picking on Jul. 24, 2014. The fruit is uniformly medium in size, mostly red in skin color with moderate freckling, clingstone in type, globose to oblate in shape, mostly orange in flesh color, firm in texture, typically 19 brix, and good in flavor.

DRAWING

The accompanying photograph consists of four whole fruits positioned to display the characteristics of the skin color and form, two half fruits divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 27, 2014, on a grafted tree during its sixth growing season. The flower and bud descriptions were developed during the previous blooming season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: Unknown plum (unpatented).
Pollen parent: Unknown interspecific *prunus* species.

TREE

Size: Medium, reaching a height of 8' [2.44 m.] and a spread of 4' [1.22 m.] after six growing seasons utilizing typical dormant pruning.
Vigor: Medium to weak, responding typically to irrigation and fertilization. The variety grows about 2' [0.61 m.] of surplus top-growth during the spring and summer. The plant should be grown on a standard commercial rootstock for production purposes.
Growth: Spreading and drooping.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive, thinning usually necessary.
Fertility: Self-unfruitful, requiring cross pollination by a suitable late seasonal blooming apricot, interspecific, or plum, such as 'Plumred VI' (U.S. Plant Pat. No. 21,051) interspecific tree.
Bearing: Regular bearer, with no crop failures observed.
Trunk:
- *Size.*—Medium, reaching a maximum diameter of 3" [76.2 mm.] after the sixth growing season.
- *Texture.*—Medium shaggy.
- *Bark Color.*—A Dark grayish yellowish brown [81. d.gy.yBr] and Dark brown [59. d.Br] variegation.
- *Lenticels.*—Approximate Number Per Square Inch: 8. Color: Deep orange yellow [69. deep OY]. Average Size: 5/16" [7.9 mm.] in length. Width is typically one fourth as much as the length. Shape: Elongated, eye-shaped.

Branches:
- *Size.*—Medium to small, diameter of the scaffold is 2" [50.8 mm.] measured 12" above the crotch reducing to ¾" [19.1 mm.] measured 12" above the first fork.
- *Texture.*—Medium shaggy.
- *Color.*—1st Year Wood Topside: Moderate reddish brown [43. m.rBr]. 1st Year Wood Underside: Brilliant yellow green [116. brill.YG]. 2nd Year Wood: Moderate reddish brown [43. m.rBr]. 3rd Year and Older Wood: A Strong brown [55. s.Br] and Grayish brown [61. gy.Br] variegation.
- *Lenticels.*—Number Per Square Inch: About 120 on second year wood. Color: Strong orange [50. s.O]. Average Size: Small, 1/16" [1.6 mm.] in length. Width is typically one fourth as much as the length. Shape: Rectangular, elongated.

Leaves:
- *Size.*—Medium. Average Length: 3⅞" [98.4 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Acute with an average angle base angle of 70 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Brilliant yellow green [116. brill.YG].
- *Petiole.*—Average Length: ½" [12.7 mm.]. Average Thickness: 1/16" [1.6 mm.]. Color: Strong reddish brown [40. s.rBr] on topside, Light yellow green [119. l.YG] on the underside.
- *Stipules.*—Number: 2 per leaf, up to 6 per growing tip. Average Length: ¼" [6.4 mm.]. Color: Moderate reddish brown [43. m.rBr].
- *Glands.*—Number: Mostly 2 per leaf. Position: Alternately positioned at the intersection of the petiole and the leaf blade. Size: Small, 1/64" [0.4 mm.] in diameter. Form: Globose. Color: Moderate yellow [87. m.Y] acquiring a Moderate olive brown [95. m.OlBr] center with age. Leaf buds: Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically about thirty stamens, five sepals and petal locations alternately positioned.
- *Average flower diameter.*—1⅛" [28.6 mm.].
- *Average flower depth.*—⅜" [9.5 mm.] when fully open.
- *Number of petals.*—Five, no double blossoms observed.
- *Petal shape.*—Oval to circular.
- *Petal margin.*—Entire, slightly wavy.
- *Average petal diameter.*—9/16" [14.3 mm.].
- *Average petal length.*—⅝" [15.9 mm.].
- *Average flower depth.*—⅜" [9.5 mm.] when fully open.
- *Petal apex.*—Rounded.

*Petal base.*—Obtuse.
*Petal color.*—White [263. White] on both sides.
*Anther color.*—Brilliant yellow [83. brill.Y].
*Stigma color.*—Light greenish yellow [101. l.gY].
*Stigma position.*—Typically located about 1/16" [1.6 mm.] above the nearby anthers.
*Sepal color.*—Brilliant yellow green [116. brill.YG] on the outer surface, Pale yellow green [121. p.YG] on the inner surface.
*Sepal length.*—7/32" [5.6 mm.].
*Sepal width.*—5/32" [4.0 mm.].
*Sepal apex.*—Rounded to elliptical to match the width and length.
*Sepal margin.*—Fairly smooth to the naked eye, slightly serrated when magnified.
*Average pistil length.*—9/16" [14.3 mm.].
*Average stamen length.*—9/16" [14.3 mm.].
*Fragrance.*—Moderate.
*Pollen production.*—Moderate, average bee enticement.
*Blooming period.*—Late, blooms about two days after 'Plumred VI' interspecific tree (U.S. Plant Pat. No. 21,051).
*Onset of bloom.*—One percent on Feb. 26, 2014.
*Date of full bloom.*—Mar. 8, 2014.
*Duration of bloom.*—One to two weeks, dependent on ambient temperature.
*Bloom density.*—Moderate.
*Number per cluster.*—2 to 8, mostly 2.

FRUIT

Maturity when described: Firm ripe, Jul. 27, 2014.
Date of first picking: Jul. 24, 2014.
Date of last picking: Aug. 3, 2014.
Size: Uniform, medium.
*Average diameter axially.*—2¼" [57.2 mm.].
*Average diameter across cheek plane.*—2 9/16" [65.1 mm.].
*Average diameter across suture plane.*—2⅝" [66.7 mm.].
*Typical weight.*—5.5 ounces [156 grams].
Form: Uniform, globose to oblate, compressed axially, mostly symmetrical.
*Longitudinal section form.*—Oblate.
*Transverse section through diameter.*—Round.
Suture: An inconspicuous Light orange yellow [70. l.OY] line located in a shallow groove extending from the base to the apex.
Ventral surface: Rounded, slightly lipped toward the apex on both sides.
Lips: Usually equal.
Cavity: Flaring, circular, suture showing on one side.
*Depth.*—½" [12.7 mm.].
*Breadth.*—1" [25.4 mm.].
Base: Truncate, slightly cordate if viewed parallel to the suture.
Apex: Truncate, slightly cordate if viewed parallel to the suture.
Pistil point: An inconspicuous Light yellow [86. l.Y] dot.
Stem: Small.
*Average length.*—⅜" [9.5 mm.].
*Average width.*—⅛" [3.2 mm.].
Skin:
*Thickness.*—Medium.
*Surface.*—Smooth.
*Tenacity.*—Tenacious to the flesh.
*Astringency.*—Very slight.
*Tendency to crack.*—None observed in dry seasons.
*Color.*—Dark red [16. d.R] over a Moderate red [15. m.R] background, small Light orange yellow [70. l.OY] areas where sun protected, Pale orange yellow [73. p.OY] freckling throughout.
*Bloom.*—Moderate.
Flesh:
*Color.*—Strong reddish orange [35. s.rO] toward the skin smoothly blending to Light orange [52. l.O] toward the stone.
*Surface of pit cavity.*—Covered with Moderate reddish orange [37. m.rO] broken fibers when twisted away from stone.
*Amygdalin.*—Scarce.
*Juice.*—Moderate, rich.
*Texture.*—Firm, crisp, meaty.
*Fibers.*—Few, fine, tender.
*Ripens.*—Fairly even, slightly earliest at apex.
*Flavor.*—Mildly acidic, sweet, typically 19 brix.
*Aroma.*—Scarce.
*Eating quality.*—Good.

STONE

Type: Clingstone.
Form: Oval.
Hilum: Narrow, oblong.
Base: Rounded.
Apex: Obtuse.
Sides: Equal.
Surface: Fairly smooth throughout with ridges on each side of the dorsal fin.
Ridges: Rounded.
External color of stone: Moderate yellowish brown [77. m.yBr] when first removed.
Pit wall color when cracked: Light yellowish brown [76. l.yBr].
Cavity surface color: Strong yellowish brown [74. s.yBr].
Average pit wall thickness: 3/32" [2.4 mm.].
Average width: ⅝" [15.9 mm.].
Average length: ⅞" [22.2 mm.].
Average breadth: ⅜" [9.5 mm.].
Tendency to split: None.
Kernel:
*Form.*—Oval.
*Skin color.*—Light orange yellow [70. l.OY] when first removed.
*Pellicle color.*—Deep yellowish brown [75. deep yBr].
*Vein color.*—Light yellowish brown [76. l.yBr].
*Taste.*—Bitter.
*Viable.*—Yes.
*Average width.*—5/16" [7.9 mm.].
*Average length.*—½" [12.7 mm.].
*Amygdalin.*—Moderate.

USE

Market: Fresh market and long distance shipping.
Keeping quality: Good, fruit quality observed to remain in good condition after 30 days in standard cold room at 36° Fahrenheit [2° Celsius].

Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Plumred VI' (U.S. Plant Pat. No. 21,051) interspecific tree, by being self-unfruitful, by blooming during the late season, and by producing fruit that is mostly globose in shape, clingstone in type, medium in size, good in flavor, and red in skin color, but is distinguished therefrom by producing fruit that is mostly orange instead of red in flesh color and that matures about fourteen days later.

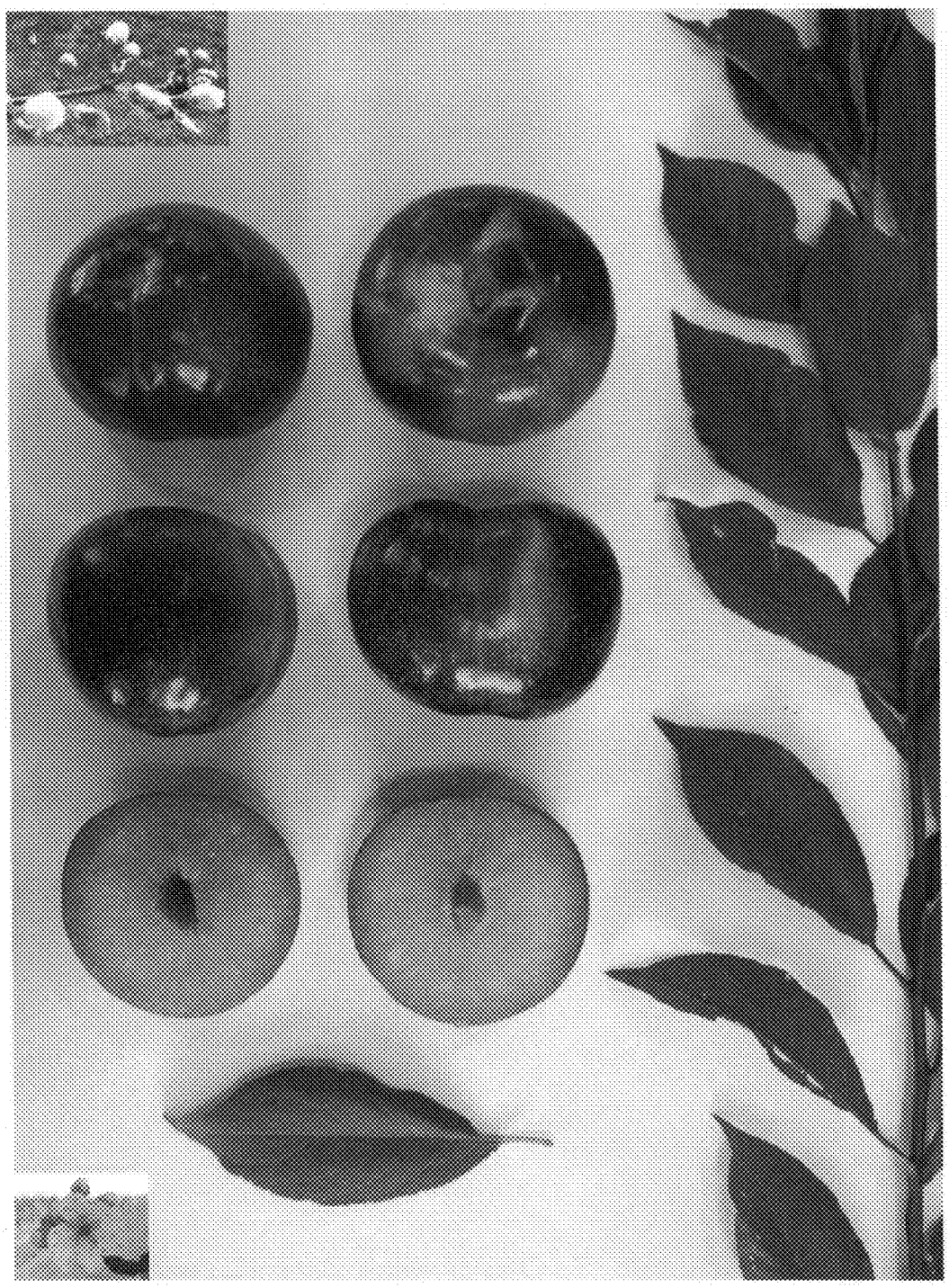

* * * * *